United States Patent [19]

Kuehne

[11] 4,362,739

[45] Dec. 7, 1982

[54] PYRROLO(2,3-d)CARBAZOLE DERIVATIVES, COMPOSITIONS AND USE

[75] Inventor: Martin E. Kuehne, Burlington, Vt.

[73] Assignee: S.A. Omnichem, Louvain-la-Neuve, Belgium

[21] Appl. No.: 260,415

[22] Filed: May 4, 1981

[51] Int. Cl.³ ................... C07D 487/10; A61K 31/40
[52] U.S. Cl. .................................. 424/274; 548/407; 548/421
[58] Field of Search ........................ 260/315; 424/274

[56] References Cited

U.S. PATENT DOCUMENTS 3,015,661 1/1962 Georgian ............................. 260/315

Primary Examiner—Robert W. Ramsuer
Attorney, Agent, or Firm—Alexis Barron

[57] ABSTRACT

This invention relates to alkyl pyrrolo(2,3-d) carbazole-6-carboxylates having antianoxic, psychotropic and hemodynamic properties and to addition salts thereof; and to preparation of the same by a synthesis sequence starting from a tryptamine and a 3-halopyruvate and involving a rearrangement of an addition compound with an aldehyde, said rearrangement being effected by Nb-alkylation of the aforementioned addition compound; and to pharmaceutical compositions containing the same; and to tetrahydroazepinoindoles used in the preparation of the same.

19 Claims, No Drawings

PYRROLO(2,3-d)CARBAZOLE DERIVATIVES, COMPOSITIONS AND USE

FIELD OF THE INVENTION

Important efforts have been devoted to the total synthesis of natural alkaloids and some of their derivatives which are therapeutic agents, particularly cerebro-vascular vasodilators or antineoplastic bis-indole alkaloids.

The present invention relates to novel pyrrolo(2,3-d)carbazole derivatives, to the preparation thereof, and to novel methanoazepinoindole intermediates. The present invention relates also to the use of the aforementioned pyrrolocarbazole derivatives as therapeutically active agents.

REPORTED DEVELOPMENTS

There are but a limited number of reports concerning pyrrolo(2,3-d)carbazole derivatives, and there is no reference in the literature to carboalkoxy-6 pyrrolo(2,3-d)carbazoles.

Known compounds possessing the pyrrolo(2,3-d)carbazole tetracyclic skeleton are either obtained indirectly from alkaloids (P. Kh. Yuldashev and S. Yu Yunosov Chem. Abstract 7820a, 62, 1965) or as crucial intermediates in a proposed total synthesis of aspidosperma or iboga alkaloids (G. Buchi et al, J.Am. Chem. Soc. 3299, 93, 1971). On the other hand, no examples of methano(3,10b)azepino(4,5-b)indoles have been reported.

Carboalkoxy-6-pyrrolo(2,3-d)carbazoles may be viewed as derivatives of D-seco vincadifformine, vincadifformine itself being of the formula

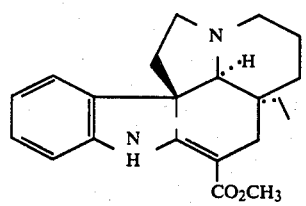

Kuehne et al have described a total synthesis of vincadifformine and numerous analogs using a synthetic process based on transformations of the azepino(4,5-b)indoles to a biogenetically postulated secodine intermediate and its cyclization to a pentacyclic aspidospermidine skeleton (J.Org.Chem. 43, 3705, 1978 and U.S. Pat. No. 4,154,943).

Several modified synthetic approaches for the generation of the secodine intermediate have also been proposed by Kuehne (U.S. Pat. No. 4,220,774, issued Sept. 2, 1980 and U.S. patent application Ser. No. 936,454, filed Aug. 24, 1979 now U.S. Pat. No. 4,267,330).

SUMMARY OF THE INVENTION

One aspect of the present invention involves pyrrolo(2,3-d)carbazole derivatives characterized by having a carboalkoxy group attached at the carbon-6 position. Such derivatives have in common the skeleton described in Formula A in which the preferred numbering is also indicated.

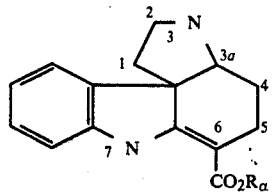

Formula A

Another aspect of the present invention involves new methano(3,10b) azepinoindoles of Formula B below and which are key precursors in the synthesis of the carbazole derivatives of the Formula A above.

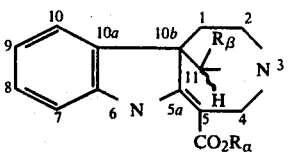

Formula B

An additional aspect of the present invention involves a synthesis in which a carboalkoxy-5-azepino(4,5-b)indole is condensed with an aldehyde to provide a methanoazepinoindole. The latter, on treatment with an alkylating reagent and in the presence of a base, yields the novel tetracyclic carboalkoxy pyrrolocarbazole derivatives of Formula A above.

Such carbazole derivatives of the present invention have been found to possess valuable pharmacological properties. Accordingly, pharmaceutical compositions including the carbazole derivatives of Formula A are also within the scope of the present invention.

It is noted also that the above-mentioned carboalkoxy-5-azepinoindole starting materials are obtained from a new process which comprises condensing a tryptamine and an alkyl 3-halopyruvate, followed by treatment with a base.

DETAILED DESCRIPTION OF THE INVENTION

Compounds of the present invention include 6 carboalkoxy-hydro-pyrrolo(2,3-d)carbazoles of the formula

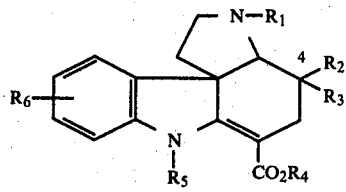

Formula I and a novel class of intermediate compounds of the formula

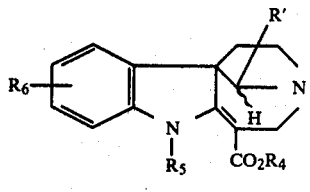

Formula II wherein:
R' represents hydrogen, phenyl or $CHR_2R_3$;

$R_1$ and $R_5$ each represents hydrogen, lower alkyl, or benzyl;

$R_2$ and $R_3$ each represents hydrogen or lower alkyl or, together, lower alkylene;

$R_4$ is lower alkyl; and $R_6$ is hydrogen, nitro, lower alkoxy, halo or hydroxy; and addition salts of said compounds. A particularly preferred class of compounds are those of Formula II in which R' is $CHR_2R_3$. Also preferred are compounds in which $R_5$ represents hydrogen or lower alkyl.

The terms "lower alkyl" and "lower alkoxy", as used herein, contemplate both straight and branched chain groups, which preferably contain 1 to about 5 carbon atoms. Exemplary preferred groups include methyl, ethyl, propyl, isopropyl, butyl, methoxy, ethoxy, propyloxy, isopropyloxy and butyloxy.

Compounds of Formulae I and II above may be provided as optical isomers, diastereomers, racemates or as a mixture of such entities. They may also be provided as acid addition salts. All such forms are within the scope of the present invention.

A process for obtaining compounds of Formula I involves, in a first step, condensing a tryptamine with an alkyl 3-halopyruvate and then treating with a base such as, for example, pyridine or a trialkylamine, to afford a 6-carboalkoxy azepinoindole of Formula III

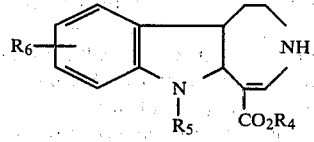

Formula III wherein $R_4$, $R_5$ and $R_6$ have the above-mentioned meanings.

Yields above 60% can be obtained.

Any suitable inert solvent may be used. It is generally preferred to employ a solvent such as, for example, an alcohol.

Exemplary starting materials, which comprise heretofore known compounds, include tryptamine, chloro-tryptamine, fluoro-tryptamine, hydroxy-tryptamine, nitro-tryptamine and methoxy-tryptamine. The substituents are preferably at position 5 or 6 of the tryptamine. Exemplary pyruvates are 3-chloro and 3-bromo pyruvates.

The novel azepinoindoles of Formula III above are obtained through the intermediacy of a α-halomethyl-α-carbo-alkoxy-β-carboline of the Formula IV below.

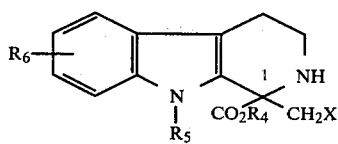

Formula IV wherein X is bromo or chloro and $R_4$, $R_5$ and $R_6$ have the above-mentioned meanings.

This carboline can be isolated and purified before adding the organic base.

Compounds of Formula IV rearrange on heating, preferably between 50° and 120° C., in the presence of a base to provide the azepinoindole of Formula III.

The use of bromopyruvate will usually give directly a mixture of the carboline of Formula IV and the azepinoindole of Formula III.

The condensation products are isolated from the reaction mixture in accordance with the standard procedures of the art. Chromatography on silica is in this respect advantageously used.

The unsaturated azepinoindole of Formula III is thereafter reduced, preferably by treatment with $NaBH_3CN$ in acetic acid or methanol/HCl, to give a compound of Formula V below.

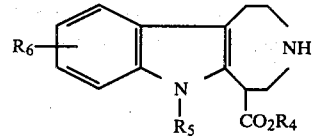

Formula V wherein $R_4$, $R_5$ and $R_6$ have the above-mentioned meanings. Other methods of reduction which have been successfully used include treatment with sodium in liquid ammonia or with zinc in aqueous sulfuric acid. Exemplary yields are between 70–90%. The aforementioned reduction methods which produce the azepinoindole of Formula V constitute a considerable improvement when compared with previous methods which involve the use of thallium or sodium dialkyl malonate (see above-mentioned U.S. Pat. No. 4,154,943). Such compounds can now be prepared in large amounts and high yields utilizing the aforementioned methods which are relatively inexpensive.

Azepinoindoles of Formula III are also key intermediates for the total synthesis of a variety of aspidospermidine alkaloids and their derivatives, for example, vincadifformine, ervinceine, N-methyl ervinceine, vindoline, pandoline, and epi-20 pandoline.

The next step in the reaction sequence for producing a pyrrolocarbazole of Formula I comprises condensing an azepinoindole of Formula V with an aldehyde of formula R''-CHO, wherein R'' is a group $R_2R_3CH$— ($R_2$, $R_3$, as defined above), to produce a methanoazepinoindole of Formula II.

In carrying out this condensation, it is generally advantageous to utilize substantially equimolar amounts of the aldehyde and of the azepinoindole of Formula V, which may be in the form of an acid addition salt, for example, a hydrochloride or a perchlorate.

The aldehyde may be present in the form of an acetal or a hemiacetal.

Optionally, a small amount of an acid catalyst, for example, benzoic acid or p-toluene sulfonic acid, may be added to the reaction medium.

The condensation can be effected conveniently in an alcohol or any other suitable solvent inert to the reaction conditions, under an inert atmosphere, preferably, $N_2$ or argon.

The reaction time may vary between about 2 hours and about 25 hours, depending on the conditions and the nature of the starting products.

The bridged azepinoindole is characterized by the usual spectroscopic methods used in organic synthesis. In particular, a characteristic β-anilino acrylate chromophore (UVλmax 299,328 nm) is present.

Isolation of the product is best achieved by dilution with ether and addition of an aqueous base, preferably aqueous ammonia, to obtain a basic aqueous layer. The organic phase can be separated in accordance with standard procedure.

After washing, filtering and concentrating under vacuum, the resulting condensation products are separated and purified by recrystallization and/or chromatography. Yields of isolated products superior to 60% are usually observed. Such yields may be as high as 95%.

When using an aldehyde of the formula $R_1CH_2—CHO$, wherein $R_1$ is not hydrogen, two condensation products are produced. These are detectable by tlc and in most cases may be differentiated using NMR techniques. The epimers with substituents at the methano carbon atom protruding over the acrylate double bond and having a less encumbered nitrogen lone pair would be expected to show lower $R_f$ values on tlc. Separation of the mixture is indeed usually best achieved using chromatographic techniques, particularly on alumina.

When using an aldehyde of the formula $R_1R_2CH—CHO$, wherein $R_1$ and $R_2$ are different substituents, four condensation products are produced. These are detectable by tlc and in most cases may be differentiated using NMR techniques.

Other aldehydes having no hydrogen atoms at the α-carbon, in particular, an aromatic aldehyde such as benzaldehyde, will also react with the azepinoindoles of Formula V to afford the corresponding bridged compounds of Formula II. Formaldehyde may also be condensed to give the C-11 unsubstituted methanoazepinoindole derivatives. These derivatives cannot be subsequently transformed into a tetracyclic compound of Formula I because of the inability of forming the required enamine moiety of the secodine-type intermediate as described hereafter.

Formation of the bridged indoloazepine products was found to be a readily reversible process. The imonium intermediate required for these reactions also gave rise to facile epimerization at the bridging carbon. While the individual pure isomers could be rapidly chromatographed on silica gel without epimerization, epimeric mixtures, containing also the indoloazepine were formed on prolonged adsorption.

Nb alkylation of the bridged azepinoindoles with an alkylating agent selected from the group consisting of lower alkyl bromide or iodide, benzyl chloride, benzyl bromide, benzyl iodide, methyl fluorosulfonate, lower alkyl methanesulfonate or trifluoromethanesulfonate resulted in the corresponding quaternary salts. It has been generally observed that one isomer of the azepinoindole, probably the one having the less hindered nitrogen lone pair, is alkylated more rapidly than its epimer. The quaternary salts retained the typical UV chromophore of the bridged azepinoindoles (λmax 299, 325), but showed a striking change of IR absorption from max 1675 and 1600 cm$^{-1}$ for one epimer to 1685, 1640 and 1600 cm$^{-1}$ for the other one. An analogous change was found for the bridged azepinoindole hydrochloride salts.

Methano(3,10-b)azepinoindolium salts can be isolated and purified in a classical way or can be employed directly without further purification for the generation of the rearranged products. It has indeed been observed that addition of tertiary amines to the N-alkylated bridged azepinoindoles derived from aldehydes having an α-proton results in their rearrangement to tetracyclic products of Formula I with a skeleton of the pentacyclic aspidosperma alkaloids lacking ring D.

Thus the generation and chemical reactivity of the previously achieved biomimetic secodine intermediates can also be demonstrated with corresponding seco intermediates of Formula VI below (Scheme I) and a versatile path to such intermediates and their cyclization products are afforded.

Scheme I

Formula II ⟶

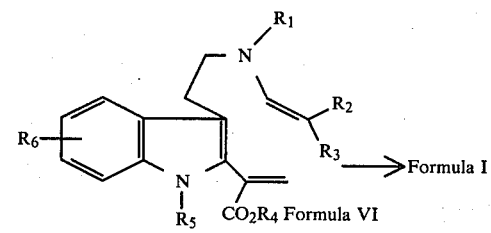

⟶Formula I wherein $R_1$, $R_2$, $R_3$, $R_4$, $R_5$ and $R_6$ have the above-mentioned meanings.

Triethylamine and diisopropylethylamine are convenient bases. Alkylation may require heating for several hours to several days in a solvent inert to the reaction conditions. Chloroform, methanol or dichlorobenzene are suitable solvents.

If desired, the N-alkyl methano azepinium salt may be isolated and possibly recrystallized and spectroscopically characterized. In this case, no base is added after alkylation has taken place.

While the bridged indoloazepines of Formula II derived from acetaldehyde and isobutyraldehyde, or any aldehyde wherein $R_2$ and $R_3$ are identical, can give only single products, (assuming a C-E ring fusion), C-4 epimeric products may be anticipated from other aldehydes which can give rise to isomeric E or Z intermediate enamines of Formula VI in the fragmentation described in Scheme I. However, only one major product is formed in the propionaldehyde and n-butyraldehyde derived cases, suggesting preferential generation and reaction of E enamine intermediates in the cases $R_2=CH_3$ or $C_2H_5$ and $R_3=H$.

If N-benzylation has been achieved, one may optionally debenzylate the resulting N-benzyl pyrrolocarbazole to the corresponding secondary amine (I, $R_1=H$). Debenzylation is performed in a classical way, preferably in acetic acid with hydrogen at atmospheric pressure in the presence of a catalyst. Such catalyst is preferably selected from the group consisting of $PtO_2$, palladium on charcoal or platinum on charcoal. The reaction is carried out until the theoretical volume of hydrogen has been absorbed. The solvent is then removed under reduced pressure and the secondary amine is recrystallized.

Optionally, the latter compound may be realkylated with an alkylating agent of choice, for example, methyl or ethyl iodide. Debenzylation, followed by realkylation, provides a way to obtain a compound of Formula I with $R_1$ being a group difficult to introduce by direct alkylation of the bridged azepinoindole.

Still optionally, compounds of Formula I wherein $R_5=H$ may be alkylated on the indole nitrogen to yield compounds wherein $R_5$ is a lower alkyl group. This alkylation is carried out using processes well known to those skilled in the art.

As mentioned above, the compounds of the present invention may be used in the form of their acid addition salts. Such salts can be produced by conventional means, for example, by treating the free base form of the compound with a suitable organic or inorganic acid. Exemplary acids which can be used include hydrochloric, hydrobromic, sulfuric, phosphoric, nitric, benzoic, methyl sulfonic, citric and lactic acid. Of particular importance are the compounds of the invention in the form of acid addition salts formed from pharmaceutically acceptable acids.

The novel compounds of the present invention may indeed be used as therapeutically active agents. The compounds have been found by pharmacological testing procedures to have interesting antianoxic, psychotropic and hemodynamic properties.

The compounds of the invention, having both antianoxic and psychotropic activities, may be used therapeutically for treating those troubled by the problems of maintaining concentration and attention, that is, lack of vigilance, and particularly, to combat behavior problems due to cerebral vascular damage and brain sclerosis in geriatric patients. They may be used also for treating lapses of memory due to cranial injuries and for treating conditions of depression. They may also be used generally for treating cerebrovascular or cardiocirculatory diseases. For example, in the case of compound I-a" (I, $R_1=R_4=CH_3$, $R_2=R_3=R_5=R_6=H$), the antianoxic oxymetric and hemodynamic test results indicate particularly high activity. The effective therapeutic use of the compounds of Formula I is shown by these test results and other standard tests used to determine psychotropic, and cerebrovascular activities and which are accepted as being reliable in determining the clinical activity of a compound. Accordingly, these compounds can be administered to animals or humans in therapeutically effective amounts to produce beneficial effects.

For their therapeutic use, the compounds and salts of Formula I may be administered either for absorption through the digestive tract, preferably orally, in the form of capsules, tablets, pellets, dragees, cachets, solutions or suspensions or by the parenteral route as buffered sterile solutions, prepared beforehand or extemporaneously, in which the active substance, base or salt, is present in an amount, such as, for example, about 0.5 mg to about 700 mg per dosage unit. The daily dose will generally vary between about 1 mg and about 500 mg according to the disease, although higher or lower amounts may also be used depending upon the specific compound and the condition of the patient. The dose rate and frequency of administration can be individually adjusted depending upon the disorder and the condition and needs of the patient being treated, as well as the recommendation of the attending physician.

For therapeutic use, the compounds of the invention can be provided as pharmaceutical compositions containing as the active substance at least one of said compounds, optionally in admixture with other active substances, and adjuvants, diluents, vehicles or carriers, as well as dyestuffs, sweeteners, preserving agents, antioxidizers, etc . . . , which are commonly used in pharmaceuticals.

The preparation of pharmaceutical or galenical formulations is effected according to usual methods substantially consisting of incorporating or admixing the active substance or substances with the excipients and adjuvants used.

If the compounds are administered in the form of their acid addition salts, pharmaceutically acceptable acids, many of which are well known, should be used.

EXAMPLES OF PREFERRED EMBODIMENTS

The following examples show the preparation of exemplary intermediate compounds of the present invention and the preparation of exemplary compounds of the present invention derived therefrom.

EXAMPLE 1 ethyl 1,2,3,4-tetrahydro-azepino(4,5-b)indole-5carboxylate—Formula III in which $R_6=R_5=H$, $R_4=CH_3CH_2$, and hereafter referred to as "III-b".

A solution of 50 g (0.312 M) of tryptamine, and of 76.18 g (0.39 M) ethyl 3-bromopyruvate in 500 ml 3% ethanolic HCl solution was refluxed under $N_2$ for 5 h. The solvent was removed under vacuum and the residue was partitioned between 500 ml water, 500 ml brine and 500 ml ethyl acetate. The organic layer was separated and the aqueous phase was extracted twice with 500 ml ethyl acetate. The organic phases were combined and dried over $MgSO_4$. Concentration under vacuum afforded a black oil (100 g). The oil was separated between 1 liter of a 5% aqueous solution of methanesulfonic acid and 600 ml of $CH_2Cl_2$, and the resulting two phases were treated separately, as follows:

(a) The organic layer was separated, concentrated under vacuum and treated with 500 ml of diethylether and 500 ml of a 5% aqueous solution of HCl. The new organic phase was again separated and dried over $MgSO_4$. Removal of the solvent gave 31.4 g of a residue which crystallized in ethanol to give 7.7 g of pure III-b.

(b) The aqueous phase was made basic with concentrated $NH_4OH$ and extracted several times with $CH_2Cl_2$. After concentration, the residue was refluxed for 3 h in pyridine. Pyridine was distilled off under reduced pressure and the residue was treated with 600 ml of a 3% aqueous solution of HCl and 600 ml of diethylether. After filtration of this mixture, the aqueous layer was separated and extracted three times with diethylether. The combined organic phases were washed with brine and dried over $Na_2SO_4$. Concentration in vacuo and crystallization in methanol gave 30 g of III-b (total yield 47%).

Mass spectrum: 256 (M+), 210 (56%), 154 (76%)

NMR ($CDCl_3$): 1.53 (t, 3H), 3.20 (m, 4H), 4.16 (q, 2H), 5.06 (m, 1H) 7.00 (m, 4H), 7.56 (d, 1H), 10.6 (s, 1H).

IR ($CHCl_3$): 3457, 3415, 3000, 1665, 1620, 1610

EXAMPLE 2

1-chloromethyl-1-carbomethoxy-1,2,3,4-tetrahydro-9H-pyrido(3,4-b)indole-Formula IV wherein X=Cl, $R_4=CH_3$, $R_5=R_6=H$, and hereafter referred to as "IV-a".

A suspension of 108.4 g (0.55 mol) of tryptaminehydrochloride in 1 liter of dry methanol and 93.2 g (0.68 mol) of methyl-3-chloropyruvate* was refluxed under $N_2$ for 24 h. The cooled mixture was poured into brine, made basic with ammonium hydroxide and extracted with dichloromethane. Concentration and trituration with ethyl acetate gave 94.0 g (61.3%) of the chloromethyl tetrahydro-β-carboline, melting point ("mp") 123°–125° C. The product was recrystallized from dichloromethane/pentane.

NMR (DCCl$_3$): δ2.80 (t, 2H), 3.02 (s, 1H), 3.24 (t, 2H), 3.81 (d, J=11 Hz, 1H) 3.87 (s, 3H), 4.26 (d, J-=11 Hz, 1H), 7.08–7.68 (m, 4H), 8.44 (s, 1H);

IR (CHCl$_3$): ν$_{max}$ 3460, 3010, 2950, 2820, 1735, 1450, 1430, 1300 cm$^{-1}$; MS (70 eV) m/e (%) 278 (15) M$^+$, 242 (66), 229 (66), 219 (100).

*A. J. Speciale and L. R. Smith, 27, J. Org. Chem., 4361 (1962).

EXAMPLE 3 methyl 1,2,3,4-tetrahydro-azepino(4,5-b)indole-5-carboxylate—Formula III in which R$_4$=CH$_3$, R$_5$=R$_6$=H, and hereafter referred to as "III-a".

A solution of 0.229 g (0.82 mmol) of the chloromethyltetrahydro-β-carboline (IV-a of Example 2) in 5 ml of dry pyridine was heated at 105° C. for 2 h under argon. The mixture was cooled and concentrated at 60° C. under vacuum. The residue was chromatographed on silica, eluting with dichloromethane. Recrystallization of the product from 2% dichloromethane in hexane gave 0.198 g (quantitative yield) of III-a, mp 138°–139° C. A reaction with 10 g of the carboline (IV-a) and 75 ml of pyridine gave a 54% yield.

NMR (CDCl$_3$) δ1.30 (bs, 1H), 3.00 (t, J=6 Hz, 2H), 3.34 (dt, J=9 Hz, 6 Hz 2H), 3.72 (s, 3H), 6.96–7.48 (m, 4H), 7.54 (d, J=9 Hz, 1H), 10.40 (s, 1H);

UV (MeOH) λ$_{max}$ 220, 242, 264, 291, 310, 343 nm; I.R. ν$_{max}$ 1600 cm$^{-1}$;

MS (70 eV) m/e (%) 243 (18) μ+1, 242 (100) M$^+$, 241 (9), 211 (9), 210 (38), 209 (18), 183 (9), 182 (18), 181 (18), 155 (15), 154 (60), 153 (15), 149 (9).

Anal. Calcd for C$_{14}$H$_{13}$N$_2$O$_2$: C, 69.40%; H, 5.81%; N, 11.56%. Found: C, 69.18%; H, 5.86%; N, 11.33%.

EXAMPLE 4 ethyl 1,2,3,4,5,6-hexahydro-azepino(4,5-b)indole-5-carboxylate—Formula V in which R$_6$=R$_5$=H, R$_4$=CH$_3$CH$_2$, and hereafter referred to as "V-b".

18.5 g (0.294 M) of NaBH$_3$CN was added to a suspension of 37.7 g (0.147 M) of the azepinoindole III-b in 350 ml of acetic acid. The solution was stirred at room temperature ("RT") for 20 h. After addition of 500 ml of CH$_2$Cl$_2$, the solution was made basic with a saturated aqueous solution of K$_2$CO$_3$. The organic layer was separated and extracted with CH$_2$Cl$_2$. The combined organic phases were washed with brine and dried over Na$_2$SO$_4$. Concentration under vacuum gave 35 g of residue which crystallized from ethyl acetate. 28 g of the azepinoindole V-b was isolated (yield 74%).

Mass spectrum: 258 (M$^+$, 63%), 216 (100%)
IR (KBr): 1725 cm$^{-1}$
NMR (CDCl$_3$): 1.23 (t, 3H), 2.18 (s, 1H), 2.70–3.20 (m, 4H), 3.20–3.53 (m, 2H), 3.73 (m, 1H), 4.13 (q, 2H), 6.83–7.53 (m, 4H), 8.33 (s, 1H)

EXAMPLE 5 methyl 1,2,3,4,5,6-hexahydro-azepino(4,5-b)indole-5-carboxylate—Formula V in which R$_5$=R$_6$=H, R$_4$=CH$_3$ and hereafter referred to as "V-a".

Following the procedure described in Example 4 and using an equivalent amount of tetrahydroazepinoindole III-a, there was obtained the corresponding hexahydroazepinoindole V-a in 80% yield, identical with an authentic sample (1) (M. E. Kuenne, D. M. Roland, R. Hafter, 43 J. Org. Chem 3705 (1978)

EXAMPLE 6 methyl 9-chloro-1,2,3,4,5,6-hexahydro-azepino(4,5-b)indole-5-carboxylate—Formula V in which R$_4$=CH$_3$, R$_5$=H, R$_6$=Cl, and hereafter referred to as "V-c".

Following the procedures described in Examples 2, 3 and 4 and using 5-chlorotryptamine as the starting material, there was obtained the corresponding chloroazepinoindole V-c (yield: 43%).

Mass spectrum: 278.5 (M+)
NMR (CDCl$_3$): 2.16 (s, 1H), 2.66–3.93 (m, 7H), 3.70 (s, 3H) 7.06 (m, 2H), 7.36 (1s, 1H), 8.23 (1H)
mp: 168°–170° C.

EXAMPLE 7 methyl 1,2,4,6-tetrahydro-11-methyl-3,5b-methanoazepino (4,5-b)indole-5-carboxylate—Formula II wherein R'=CHR$_2$R$_3$, R$_2$=R$_3$=R$_5$=R$_6$=H, R$_4$=CH$_3$.

A 3% methanolic HCl solution was added to 500 mg (2.05 mmol) of the indoloazepine monoester V-a in 5 ml of dry methanol until the solution was strongly acidic. The methanol and excess HCl were removed under vacuum and the residual amine hydrochloride was dissolved in 5 ml of water. To this solution was added 0.51 ml of methanol containing 113 mg (2.60 mmol) of acetaldehyde. After stirring for 8 h at 22° C. the reaction mixture contained a trace of indoloazepine seen by thin layer chromatography ("tlc") (SiO$_2$, 5% methanol in dichloromethane) R$_f$0.1, and two isomeric products, hereinafter referred to as "II-a" and "II-a'", R$_f$ 0.20–0.25 which all stained blue with ceric ammonium sulfate ("CAS") spray. The reaction mixture was diluted with 20 ml of ether and aqueous ammonia was added dropwise with rapid stirring until the aqueous layer was strongly basic. The phases were separated and the aqueous layer extracted with 15 ml of ether. The ether solutions were combined and washed with water (2×25 ml) and brine (25 ml), dried (Na$_2$SO$_4$), filtered and concentrated under vacuum to yield 0.502 g (91%) of the amorphous condensation products II-a and II-a' in a ratio of 3:2 as determined by NMR (below). The product mixture crystallized from ether with variable melting points. Separation of the mixture on alumina (neutral, activity II) by elution with ether gave the more polar product II-a, mp 149°–151° C.: NMR (CDCl$_3$) δ9.33 (1H, bs), 7.58–7.0 (4H, m), 4.17-3.3 (4H, m), 3.2–2.8 (1H, bm), 2.5–2.05 (2H, m), 1.05 (3H, d, J5 Hz); IR (KBr) ν$_{max}$ 3400, 2910, 2840, 1675, 1605, 1460, 1430, 1280, 1270, 1240, 1175, 1140, 1030, 760, 725 cm$^{-1}$; UV (MeOH) λ$_{max}$ 225, 295, 327 nm; mass spectrum (80 eV) m/e (%) 271 (21), 270 (100), 215 (42), 214 (90), 155 (21), 154 (64), 127 (21), 56 (43).

Anal. Calcd for C$_{16}$H$_{18}$N$_2$O$_2$: C, 71.09%; H, 6.71%; N, 10.37%;

Found: C, 77.24%; H, 6.82%; N, 10.22%.

The less polar product II-a' crystallized from cyclohexane, had mp 144°–145° C; NMR (CDCl$_3$) δ9.45 (1H, bs), 7.78–7.0 (4H, m), 4.34-3.5 (6H, m), 3.45–2.81 (2H, m), 2.49 (2H, t, J8 Hz), 1.52 (3H, d, J5 Hz); IR (KBr) ν$_{max}$ 3400, 2930, 2860, 1675, 1605, 1460, 1435, 1270, 1240, 1230, 1185, 1035, 775, 750, 740, 728 cm$^{-1}$; UV λ$_{max}$ 225, 295, 327 nm; mass spectrum (80 eV) m/e (%) 271 (22), 270, (100), 215 (46), 214 (89), 155 (23), 154 (64), 127 (21), 56 (42).

Anal. Calcd. for C$_{16}$H$_{18}$N$_2$O$_2$: C, 71.09%; H, 6.71%;, N, 10.37%;

Found: C, 71.35%; H, 6.88%;, N, 10.18%. EXAMPLE 8 methyl 1,2,4,6-tetrahydro-11-phenyl-3,5b-methanoazepino(4,5-b) indole-5-carboxylate—Formula II wherein R'=phenyl, $R_5=R_6=H$, $R_4=CH_3$.

A mixture of 200 mg (0.82 mmol) of the indoloazepine V-a and 96.7 mg (0.90 mmol) of benzaldehyde in 5 ml of dry methanol was stirred for 8 h. After concentration under vacuum, tlc of the residue (SiO$_2$, 5% methanol in dichloromethane) showed two products with R$_f$ 0.5 and 0.7, and a trace of starting amine with R$_f$ 0.1, all staining blue with CAS spray. The two isomeric products, hereafter referred to as "II-b", and "II-b'", were present in a ratio of 2:1 (judged by NMR, below). Frictional crystallization from ether or cyclohexane gave the more polar isomer II-b:mp 148°–150° C.; NMR (CDCl$_3$) δ9.19 (1H, bs), 7.46–6.90 (9H, m), 4.69 (1H, s), 3.85–3.67 (4H, m, includes—OCH$_3$, 3H, s at 3.66), 2.47 (2H, m); IR (KBr) $\nu_{max}$ 3380, 3310, 2890, 2850, 1675, 1600, 1460, 1425, 1380, 1290, 1245, 1225, 1180, 1045, 800, 770, 750, 735, 730, 690; UV (MeOH) $\lambda_{max}$ 210, 225 (sh), 300, 330; mass spectrum (80 eV) m/e (%) 333 (29), 332 (96), 215 (51), 214 (100), 182 (21), 155 (22), 154 (73), 91 (37).

Anal. Calcd. for C$_{21}$H$_{20}$N$_2$O$_2$: C, 75.88%; H, 6.07%; N, 8.43%. Found: C, 75.93%; H, 6.28%; N, 8.26%.

Separation of 164 mg (60%) of the isomeric products, obtained by filtration of a 1:3 dichloromethane/ether solution of the reaction concentrate (generated above) through alumina, by chromatography on alumina (neutral, activity I) and eluting with ethyl acetate/hexane (1:1), gave the less polar isomer II-b': mp 156°–158° C.; NMR (CDCl$_3$) δ 9.26 (1H, s), 7.64–6.60 (8H, m), 6.36 (1H, d, J8), 4.28–3.48 (7H, m, includes —OCH$_3$, 3H, s, at 3.72 and 1H, s at 4.16), 3.20–2.76 (2H, m); IR (KBr) $\nu_{max}$ 3380, 2960, 2900, 2855, 1670, 1605, 1460, 1435, 1285, 1235, 1190, 1050, 1025, 780, 755, 740, 725, 705; UV (MeOH) $\lambda_{max}$ 227, 229, 328 nm; mass spectrum (80 eV) m/e (%) 333 (31), 332 (97), 215 (48), 214 (100), 182 (18), 154 (65), 137 (18), 91 (46).

Anal. Calcd. for C$_{21}$H$_{20}$N$_2$O$_2$: C, 75.88%; H, 6.07%; N, 8.43%. Found: C, 75.85%; H, 6.23%; N, 8.40%.

EXAMPLE 9 methyl 1,2,4,6-tetrahydro-3,5b-methanoazepino(4,5-b)indole-5-carboxylate—Formula II wherein R'=H, $R_5=R_6=6$; $R_4=CH_3$ A solution of 50 mg (1.67 mmol) of paraformaldehyde and a crystal of KOH in 2 ml of methanol was added to 150 mg (0.614 mmol) of the indoloazepine V-a in 5 ml of methanol. After stirring for 5 h at 22° C. under nitrogen tlc (SiO$_2$, 5% methanol in dichloromethane) showed no starting amine but a less polar product with R$_f$ 0.2 which stained blue with CAS spray. Concentration under vacuum and filtration of an ether solution of the residue through neutral alumina, concentration and crystallization from ether-hexane gave 0.15 g (95%) of product, hereafter referred to as "II-c", with mp 147°–150° C.; 250 MHz NMR (CDCl$_3$) δ 8.91 (1H, bs), 7.31–6.82 (4H, m), 3.98 (1H, d, J16 Hz), 3.86 (3H, s), 3.41 (2H, m), 3.20 (1H, d, J12 Hz), 2.92 (2H, m), 2.44–2.12 (2H, m); IR (KBr) $\nu_{max}$ 3400, 1675, 1605 cm$^{-1}$; UV (MeOH) $\lambda_{max}$ 230, 297, 329 nm; mass spectrum (80 eV), m/e (%) 257 (29), 256 (100), 215 (48), 214 (87), 155 (28), 154 (66), 128 (28), 127 (28).

Anal. Calcd. for C$_{15}$H$_{16}$N$_2$O$_2$: C, 70.29%; H, 6.29%; N, 10.93%. Found: C, 70.54%; H, 6.38%; N, 10.80%.

EXAMPLE 10 methyl 11-ethyl-1,2,4,6-tetrahydro-3,5b-methanoazepino(4,5-b)indole-5-carboxylate—Formula II wherein R'=CHR$_2$R$_3$, R$_2$=CH$_3$, R$_3$=R$_5$=R$_6$=H, R$_4$=CH$_3$ From 200 mg (0.82 mmol) of indoloazepine and 52.4 mg (0.90 mmol) of propionaldehyde in 5 ml of methanol at 22° C. two isomeric products, hereafter referred to as "II-d" and "II-d'", obtained after 8 h, had R$_f$ 0.26 and 0.48 (SiO$_2$, 5% methanol in dichloromethane), detected with CAS (blue). NMR analysis of the mixture indicated at 2:1 product ratio in favor of the more polar isomer II-d. Fractional crystallization from ether gave the more polar isomer II-d; mp 157°–158° C. Chromatographic separation of the isomers by preparative tlc on Al$_2$O$_3$ with ether gave the less polar isomer II-d' as a non-crystalline solid. For the more polar isomer II-d: NMR (CDCl$_3$) δ 8.89 (1H, bs), 7.30–6.75 (4H, m), 3.96–3.65 (4H, m includes —OCH$_3$ at 3.73, 3H, s), 3.45–2.72 (4H, m), 2.39–2.15 (2H, m), 1.48–1.16 (2H, m), 0.88 (3H, t, J7 Hz); IR (KBr) $\nu_{max}$ 3360, 2940, 2850, 1680, 1610, 1465, 1435, 1295, 1240, 1180, 1045, 1015, 880, 805, 780, 760, 745, 730 cm$^{-1}$; UV (MeOH) $\lambda_{max}$ 230, 300, 327 nm; mass spectrum (80 eV) m/e (%) 285 (54), 284 (99), 215 (71), 214 (100), 182 (46), 154 (79), 127 (43), 70 (54).

Anal. Calcd. for C$_{17}$H$_{20}$N$_2$O$_2$: C, 71.80%; H, 7.09%; N, 9.85%. Found: C, 71.71%; H, 7.17%; N, 9.59%.

For the less polar isomer II-d': NMR (CDCl$_3$) δ 9.02 (1H, bs), 7.34–6.75 (4H, m), 4.08–3.85 (1Hd, J16 Hz), 3.74 (3H, s), 3.60–3.15 (2H, m), 2.96–2.64 (2H, m), 2.39–2.15 (2H, m), 1.95–1.61 (2H m), 1.03 (3H, t, J7 Hz); IR (KBr) $\lambda_{max}$: 3360, 2920, 2860, 1675, 1605, 1465, 1435, 1365, 1285, 1235, 1190, 1040, 780, 745 cm$^{-1}$; UV(MeOH) $\lambda_{max}$, 230, 300, 327 nm; mass spectrum (80 eV), m/e (%) 285 (42), 284 (100), 215 (74), 214 (99), 182 (36), 154 (78), 127 (34), 70 (52).

EXAMPLE 11 methyl 1,2,4,6-tetrahydro-11-isopropyl-3,5b-methanoazepino(4,5b)indole-5-carboxylate—Formula II wherein R'=CHR$_2$R$_3$, R$_2$=R$_3$=R$_4$=CH$_3$, R$_5$=H, and hereafter referred to as "II-e"

A solution of 250 mg (1.02 mmol) of the indoloazepine V-a, 81.3 mg (1.13 mmol) of isobutyraldehyde and a crystal of benzoic acid in 10 ml of dry methanol was stirred under nitrogen at 50° C. for 14 h. tlc (SiO$_2$, 5% methanol in dichloromethane) then showed two products, R$_f$ 0.7 and 0.3, detected with CAS spray (blue), with the more polar component predominating. Concentration under vacuum and recrystallization of the crystalline residue from methanol gave 174 mg of the lower R$_f$ component II-e which was recrystallized from ether/hexane, mp 157°–158° C. Chromatography of the initial methanolic mother liquors on silica gel, elution with 2.5% methanol in dichloromethane and crystallization from ether/hexane gave an additional 36 mg of the more polar product II-e (total yield 70%): NMR (CDCl$_3$) δ 9.31 (1H, bs), 7.58–7.02 (4H, m), 4.02 (1H, d, J17 Hz), 3.88 (3H, s), 3.8–3.3 (3H, m), 3.18–2.28 (3H, m), 2.5–2.6 (2H, m), 1.98–1.66 (1H, m), 1.13 (3H, d, J7 Hz), 0.43 (3H, d, J7 Hz); IR (KBr) $\nu_{max}$ 3390, 3310, 2900, 2860, 1605, 1460, 1430, 1290, 1245, 1225, 1180, 1050, 775, 750, 740, 730, 695 cm$^{-1}$; UV (MeOH) $\lambda_{max}$ 225, 300, 327; mass spectrum (80 eV) m/e (%) 299 (49), 298 (99), 215 (67), 214 (100), 167 (30), 155 (33), 154 (78), 84 (57).

Anal. Calcd. for $C_{18}H_{22}N_2O_2$: C, 72.45%; H, 7.43%; N, 9.39; Found: C, 72.69%; H, 7.51%; N, 9.37%.

EXAMPLE 12 methyl 1,2,4,6-tetrahydro-11-propyl-3,5b-methanoazepino(4,5-b)indole-5-carboxylate—Formula II wherein $R'=CH_2R_2R_3R_2=CH_2CH_3$, $R_3=R_5=H$, $R_4=CH_3$, and hereafter referred to as "II-f"

After 18 h at 22° C., a solution of 250 mg (1.02 mmol) of the indoloazepine V-a and 77.6 (1.08 mmol) of n-butyraldehyde in 5 ml of methanol showed two products by tlc (SiO$_2$, 5% methanol in dichloromethane) $R_f$ 0.58 and 0.38, detected with CAS spray (blue) as well as some starting amine $R_f$ 0.08 (blue). The solvent was evaporated under vacuum and an ether solution of the residue filtered through neutral alumina. On concentration, 240 mg (80%) of the reaction products showed a 2:1 isomer ratio by NMR (below), in favor of the lower $R_f$ product. The isomers were separated by column chromatography (SiO$_2$, 5% methanol in dichloromethane). The lower $R_f$ isomer II-f was crystallized from ether and had: mp 144°–145° C.; NMR (CDCl$_3$) δ 8.99 (1H, s), 7.33–6.80 (4 H, m), 4.02–3.70 (4H, m contains —OCH$_3$ 3.77, 3H, s), 3.50–3.19 (3H, m) 3.09–2.70 (1H, m), 2.40–2.12 (2H, m), 1.57–1.02 (4H, m), 0.96–0.69 (3H, t); IR (KBr) $\nu_{max}$ 3340, 2930, 2860, 1680, 1610, 1460, 1430, 1290, 1240, 1180, 735 cm$^{-1}$; UV(MeOH) $\lambda_{max}$ 232, 305 (sh), 332 nm; mass spectrum (80 eV) m/e (%) 299 (34), 298 (97), 215 (64), 214 (100), 182 (24), 155 (24), 154 (72), 84 (47). Melting point of the hydrochloride: 183°–184° C.

The higher $R_f$ isomer was amorphous. NMR (CDCl$_3$) δ 9.01 (1H, s), 7.35–6.76 (4H, m), 3.95 (1H, d, J 16 Hz), 3.72 (3H, s), 3.59–3.18 (2H, m), 3.02–2.59 (2H, m), 2.37–2.14 (2H, m), 1.82–1.15 (4H, m), 1.08–0.82 (3H, t); IR (KBr) $\nu_{max}$ 3380, 2950, 2860, 1675, 1605, 1465, 1435, 1285, 1235, 1185, 1050, 1020, 800, 735; UV(MeOH) $\lambda_{max}$ 232, 305 (sh), 332 nm, mass spectrum (80 eV) m/e (%) 299 (18), 298 (84), 215 (31), 214 (100), 155 (13), 154 (51), 84 (23), 43 (29).

EXAMPLE 13 methyl 3-benzyl-1,2,3,3a,4,5-hexahydro-7H-pyrrolo(2,3-d)carbazole-6-carboxylate—Formula I wherein $R_1=CH_6H_5CH_2$, $R_2=R_3=R_5=R_6=H$, $R_4=CH_3$, and hereafter referred to as "I-a"

A solution of 150 mg (0.56 mmol) of the acetaldehyde derived product mixture of II-a and II-a', 105 mg (0.61 mmol) of benzyl bromide and 150 µl of N,N-diisopropyl ethyl amine in 5 ml of chloroform was refluxed for seven days under nitrogen. tlc (SiO$_2$, 5% methanol in dichloromethane) then showed a major product at $R_f$ 0.85 and a few minor components. Concentration under vacuum and column chromatography of the residue on silica gel gave nonpolar components with 50 ml of dichloromethane followed by 91 mg (45%) of the major product I-a, eluted with 5% ether in dichloromethane. A sample recrystallized from methanol had mp 58°–60° C.; NMR (CDCl$_3$) δ 9.36 (1H, bs), 7.85–7.03 (9H, m), 4.25 (1H, d, J 12 Hz), 4.08–3.80 (4H, m, includes —OCH$_3$ at 3.99, 3H, s), 3.67 (2H, s), 3.48 (1H, d, J=4 Hz), 3.19–1.20 (6H, bm); IR (KBr) 3390, 2910, 2810, 1670, 1605, 1465, 1435, 1275, 1250, 1235, 1180, 1025, 750 cm$^{-1}$; UV (MeOH) $\lambda_{max}$ 220, 292, 329; mass spectrum (80 eV) m/e (%) 361 (46), 360 (98), 228 (74), 227 (100), 167 (62), 154 (51), 146 (83), 91 (79).

Anal. Calcd. for $C_{23}H_{24}N_2O_2$: C, 76.64%; H, 6.71%; N, 7.77%. Found: C, 76.42%; H, 6.84%; N, 7.57%.

EXAMPLE 14 methyl 1,2,3,3a,4,5-hexahydro-7H-pyrrolo(2,3-d)carbazole-6-carboxylate—Formula I wherein $R_1=R_2=R_3=R_5=R_6=H$, $R_4=CH_3$, and hereafter referred to as "I-a'"

Hydrogenolysis of 180 mg (0.50 mmol) of I-a in 5 ml of acetic acid with 36 mg of 10% palladium on carbon catalyst at atmospheric pressure was continued until 1.2 equivalents of hydrogen were absorbed. The solution was filtered, the flask and filter rinsed with 5 ml of methanol and the combined filtrates poured into a solvent comprising 20 ml of water and 10 ml ether. Ammonium hydroxide was added at 0° C. with vigorous stirring until the aqueous layer was basic. The organic phase was separated, dried (Na$_2$SO$_4$), concentrated and the residue crystallized from ether/hexane to give 123 mg (91%) of I-a': mp 145°–148° C.; NMR (CDCl$_3$) δ 9.04 (1H, bs), 7.29–6.75 (4H, m), 3.76 (3H, s), 3.19–2.97 (2H, m), 2.81–2.90 (1H, m), 2.28–1.06 (7H, m); IR (KBr) $\nu_{max}$ 3305, 3200 (br), 2925, 2825, 1675, 1595, 1245, 1195, 740 cm$^{-1}$; UV (MeOH) $\lambda_{max}$ 230, 300, 329 nm; mass spectrum (80 eV) m/e (%) 270 (100), 27 (63), 215 (99), 214 (91), 182 (33), 167 (34), 154 (51), 56 (55).

A hydrochloride formed with dry HCl in ether and recrystallized from methanol/acetonitrile had mp 212°–213° C. dec.

Anal. Calcd. for $C_{16}H_{19}N_2O_2Cl$: C, 62.54%; H, 6.24%, N, 9.13%, Cl, 11.56%. Found: C, 62.64%; H, 6.52%; N, 9.09%; Cl, 11.56%.

EXAMPLE 15 methyl 1,2,3,3a,4,5-hexahydro-3-methyl-7H-pyrrolo(2,3-d)carbazole-6-carboxylate—Formula I wherein $R_1=R_4=CH_3$, $R_2=R_3=R_5=R_6=H$, and hereafter referred to as "I-a'''".

A solution of 100 mg (0.37 mmol) of the acetaldehyde derived product mixture II-a and 57.8 mg (0.41 mmol) of methyl iodide in 5 ml of chloroform was stirred under N$_2$ for 24 h. N,N-diisopropylethylamine (0.5 ml) and additional methyl iodide (6 mg, 0.04 mmol) were added and the solution was refluxed for seven days. tlc (SiO$_2$, 5% dichloromethane in methanol) showed one major product, $R_f$ 0.4, staining blue with CAS reagent. Extractive workup followed by chromatography on silica gel, eluting with ether, gave 80.7 mg (77%) of product I-a'' as an amorphous solid. NMR (CDCl$_3$) δ 9.12 (1H, bs), 7.36–6.78 (4H, m), 3.78 (3H, s), 3.12–1.34 (12H, m, includes N-Me, 2.58, s), 1.28–0.86 (1H, bm); IR (KBr) $\nu_{max}$ 3370, 2940, 2840, 2780, 1670, 1605, 1239, 1200, 1190 cm$^{-1}$; UV (MeOH) $\lambda_{max}$: 230, 297, 330 nm; mass spectrum (80 eV) m/e (%) 284 (88), 228 (45), 227 (100), 214 (52), 201 (30), 167 (30), 154 (30), 70 (81).

A hydrochloride formed with dry HCl in ether and recrystallized from acetonitrile had mp 238°–239° C. (d).

Anal. Calcd. for $C_{17}H_{21}N_2O_2Cl$: C, 63.64%; H, 6.60%; N, 8.73%. Found: C, 63.43%; H, 6.64%; N, 8.59%.

Alternatively, rearrangement product I-a″ could be formed by methylation of the secondary amine I-a′. A mixture of 50 mg (0.185 mmol) of the amine I-a′ and 1.1 equiv. of iodomethane in 2 ml of dichloromethane was stirred in the dark for 48 h. tlc ($SiO_2$, 4:1 ethyl acetate-methanol) showed two mobile spots staining blue with CAS reagent at $R_f$ 0.85 (product I-a″) and $R_f$ 0.15 (starting material I-a′) as well as a blue spot at the origin. A basic workup followed by column chromatography on silica gel, eluting with 20%–50% methanol in ethyl acetate yielded the N-methyl product as a white foam and 13.5 mg of crystalline starting material. Dissolution of the foam in dichloromethane, treatment with a solution of HCl gas in ether and subsequent crystallization from ether/acetonitrile yielded 33.1 mg of a hydrochloride (56%, 76% based on recovered starting material) which was identical by IR, UV, tlc, mp (both direct and mixture) with the hydrochloride of the product I-a″ formed above.

EXAMPLE 16 methyl 3-benzyl-1,2,3,3a,4,5-hexahydro-4-methyl-7H-pyrrolo(2,3-d)carbazole-6-carboxylate—Formula I wherein $R_2 = R_4 = CH_3$, $R_1 = C_6H_5CH_2$, $R_3 = R_5 = R_6 = H$, and hereafter referred to as "I-d".

Following the procedure of Example 13 and using 176 mg (0.62 mmol) of the propionaldehyde bridged indoloazepines II-d and II-d′ and 117 mg (0.68 mmol) of benzyl bromide and heating for 48 h after addition of 120 mg (0.93 mmol) of N,N-diisopropyl ethylamine, gave, after chromatography, 194 mg (84%) of the amorphous product I-d. NMR ($CDCl_3$) δ8.99 (1 H, bs), 7.44–6.76 (4H, m), 4.12 (1H, d, J 13 Hz), 3.81–3.62 (4H, m, includes 3.77, —$OCH_3$, 3H, s), 2.96–2.84 (2H, m), 2.73–2.50 (3H, m), 2.15–1.94 (2H, m), 1.72–1.60 (1H, m), 0.61 (3H, d, J 7 Hz); at 250 MHz δ3.75 (3H, s, —$OCH_3$), 2.89 (1H, q, H-5), 2.87 (1H, s, H-21); IR (KBr) $\nu_{max}$ 3360, 2940, 2900, 2895, 1675, 1610, 1250, 1205, 1145, 745, 705 cm$^{-1}$; mass spectrum (80 eV) m/e (%) 374 (69), 241 (100), 161 (56), 160 (94), 106 (53), 105 (55), 91 (75), 77 (54). A hydrochloride recrystallized from acetonitrile/methanol had: mp 242°–243° C.; UV (MeOH) $\lambda_{max}$ 230, 300, 327 nm.

Anal. Calcd. for $C_{24}H_{27}N_2O_2Cl$: C, 70.14%; H, 6.62%; N, 6.82%; Cl, 8.63%. Found: C, 70.00%; H, 6.90%; N, 6.81%; Cl, 8.63%.

EXAMPLE 17 methyl 3-benzyl-1,2,3,3a,4,5-hexahydro-4,4-dimethyl-7H-pyrrolo(2,3-d)carbazole-6-carboxylate—Formula I wherein $R_2 = R_3 = R_4 = CH_3$, $R_1 = C_6H_5CH_2$, $R_5 = R_6 = H$, and hereafter referred to as "I-e".

Following the procedure of Example 13 and employing 200 mg (0.671 mmol) of the amine II-e, 126 mg (0.738 mmol) of benzyl bromide and 200 μl of N,N-diisopropyl ethylamine led to a concentrate which was dissolved in 10 ml of methanol, and poured into aqueous $K_2CO_3$. Extraction with ether (3×10 ml), washing of the combined extracts with water and brine, drying over $Na_2SO_4$, concentration, column chromatography ($SiO_2$, 2.5% methanol in dichloromethane) and crystallization from methanol gave 0.18 g (69%), of I-e: mp 96°–97° C.; NMR ($CDCl_3$) δ9.08 (1H, bs), 7.62–6.78 (9H, m), 4.32 (1H, d, J 13 Hz), 3.84–3.64 (4H, m, contains —$OCH_3$ at 3.90, 3H, s), 3.08–1.88 (6H, m), 1.70–1.42 (1H, m), 1.30 (3H, s), 0.62 (3H, s); IR (KBr) $\nu_{max}$ 3400, 2950, 2840, 2790, 1675, 1605, 1460, 1435, 1280, 1245, 1205, 1185, 1165, 1110, 1040, 745 cm$^{-1}$; UV (MeOH) $\lambda_{max}$ 220, 292, 328; mass spectrum (80 eV) m/e (%) 388 (63), 175 (50), 174 (100), 144 (49), 131 (65), 130 (50), 102 (69), 91 (72).

Anal. Calcd. for $C_{25}H_{28}N_2O_2$: C, 77.29%; H, 7.26%; N, 7.21%. Found: C, 77.08%; H, 7.43%; N, 7.06%.

EXAMPLE 18 methyl 1,2,3,3a,4,5-hexahydro-4,4-dimethyl-7H-pyrrolo(2,3-d)carbazole-6-carboxylate—Formula I wherein $R_1 = R_5 = R_6 = H$, $R_2 = R_3 = R_4 = CH_3$, and hereafter referred to as "I-c′".

Hydrogenation of 80 mg (0.21 mmol) of I-e in 3 ml of acetic acid with 8 mg of 10% palladium on carbon catalyst at atmospheric pressure was stopped when 1.1 equivalent of hydrogen had been taken up. The solution was filtered, the flask and catalyst rinsed with 5 ml of methanol and the combined filtrates poured into 50 ml of water and 50 ml of ether. Ammonium hydroxide was added dropwise at 0° C. with rapid stirring until the aqueous layer was basic. The organic phase was then separated, washed with water and brine, dried ($Na_2SO_4$) and concentrated to 56 mg (91%) of the amorphous amine I-e′. A hydrochloride, formed with dry HCl in ether and recrystallized from methanol had a decomposition point ≃300° C. NMR (free base, $CDCl_3$) δ9.17 (1H, bs), 7.43–6.97 (4H, m), 3.85 (3H, s), 3.33 (1H, s), 3.16 (2H, m), 2.26 (3H, s), 1.85 (2H, m), 1.13 (3H, s), 0.57 (3H, s); IR (HCl salt, KBr) $\lambda_{max}$ 3400, 3220, 2950, 2860, 1675, 1600, 1460, 1435, 1380, 1305, 1285, 1250, 1225, 1200, 1165, 870, 750, 730, 695 cm$^{-1}$; UV (HCl salt, MeOH) $\lambda_{max}$ 225, 295, 325; mass spectrum of free base (80 eV) m/e (%) 299 (56), 298 (100), 216 (48), 215 (87), 214 (37), 154 (43), 84 (85).

Anal. Calcd. for $C_{18}H_{23}N_2O_2Cl$: C, 64.56%; H, 6.92%, N, 8.37%; Cl, 10.59%. Found: C, 64.46%; H, 7.22%; N, 8.17%; Cl, 10.70%.

EXAMPLE 18′

The corresponding ethyl ester of I-e′, ethyl 1,2,3,3a,4,5-hexahydro-4,4-dimethyl-7H-pyrrolo(2,3-d)carbazole-6-carboxylate—Formula I wherein $R_1 = R_5 = R_6 = H$, $R_2 = R_3 = CH_3$, $R_4 = CH_2CH_3$, and hereafter referred to as "I-e", was prepared.

EXAMPLE 18

Following the procedures of examples 7, 17 and 18 but using the azepinoindole V-b as starting material, I-e″ was isolated with an overall yield of 52%. IR ($CCl_4$, 3%) 3395, 2960, 1676, 1611, 1468, 1247. UV ($CH_3OH$, hydrochloride) 328 (4.23), 299 (4.07), 230 (3.95) NMR ($CDCl_3$), 0.56 (s, 3H), 118 (s, 3H), 1.30 (t, 3H), 4.16 (q, 2H).

EXAMPLE 19 methyl 4,4-dimethyl-3-ethyl-1,2,3,3a,4,5-hexahydro-7H-pyrrolo(2,3-d)carbazole-6-carboxylate—Formula I wherein $R_2=R_3=R_4=CH_3$, $R_1=CH_2CH_3$, $R_5=R_6=H$, and hereafter referred to as "I-e'''."

A solution of 10.7 g (0.036 M) of pyrrolocarbazole I-e' (Example 18), 6.7 g (0.043 M) of ethyl iodide and 5.55 g (0.043 M) of diisopropylethylamine in 150 ml of $CHCl_3$ was refluxed for 24 h. An additional 3 g of ethyl iodide and 2.5 g of diisopropylethylamine were then added and the reflux maintained for an additional 24 h. The solvent and excess reagent were removed in vacuo and the residue was treated with 300 ml of diethylether and 200 ml of aqueous $K_2CO_3$. The organic layer was separated and extracted three times with ether. The combined organic phases were washed with water and a saturated aqueous solution of NaCl and dried over $MgSO_4$. The solvent was removed in vacuo to afford an oil which crystallized in methanol. 10.14 g (yield 85%) of compound I-e''' were isolated. mp 108°-110° C.; mass spectrum 326 (M+ 25%), 112 (100%); UV ($CH_3OH$, max, log): 330 (4.09), 300 (3.91), 224 (3.81); IR ($CCl_4$): 3395, 2975, 1681, 1623, 1610, 1474, 1465 cm$^{-1}$.

EXAMPLE 20 methyl 3-benzyl-4-ethyl-1,2,3,3a,4,5-hexahydro-7H-pyrrolo(2,3-d)carbazole-6-carboxylate—Formula I wherein $R_1=C_6H_5CH_2$, $R_2=CH_3CH_2$, $R_3=R_5=R_6=H$, $R_4=CH_3$, and hereafter referred to as "I-f".

A solution of the amine II-f (129 mg, 0.43 mmol) and benzyl bromide (77 mg, 0.45 mmol) in 5 ml of chloroform was refluxed under $N_2$ for 16 h. Diisopropylethylamine (59 mg, 0.45 mmol) was added and the mixture refluxed for four days. tlc ($SiO_2$, 5% methanol in dichloromethane) then showed one product with $R_f$ 0.85, staining blue with CAS reagent. The solvent was evaporated at reduced pressure and the residue chromatographed ($SiO_2$ column, 2-3% ether in dichloromethane) to yield 158 mg (94%) of I-f as a white foam which crystallized from methanol or ether/hexane giving 150 mg (90%) of white crystals: mp 92°-94° C.; NMR ($CDCl_3$) $\delta 9.10$ (1H, bs), 7.60-6.76 (9H, m), 4.13 (1H, d, J 13 Hz), 3.84-3.60 (4H, m, includes 3.77, 3H, s), 2.93-2.42 (5H, m), 2.14-1.60 (3H, m), 0.92-0.60 (5H, m); at 250 MHz, $\delta 3.77$ (3H, s, —$OCH_3$), 2.93 (1H, s, H-21), 2.90 (1H, q, H-5); IR (KBr) $\nu_{max}$ 3370, 2900, 2800, 1670, 1608, 1260, 1245, 1235, 1195, 740, 695 cm$^{-1}$; UV (MeOH) $\lambda_{max}$ 227, 300, 327 nm; mass spectrum m/e (%) 388 (95), 256 (54), 255 (100), 175 (65), 174 (99), 167 (46), 154 (34), 91 (81).

Anal. Calcd. for $C_{25}H_{28}N_2O_2$: C, 77.29%; H, 3.26%; N, 7.21%. Found: C, 77.27%; H, 7.39%; N, 7.00%.

EXAMPLE 21 methyl 4-ethyl-1,2,3,3a,4,5-hexahydro-7H-pyrrolo(2,3-d)carbazole-6-carboxylate—Formula I wherein $R_1=R_3=R_5=R_6=H$, $R_2=CH_3CH_2$, $R_4=CH_3$, and hereafter referred to as I-f'''.

Hydrogenolysis of 150 mg (0.39 mmol) of I-f in 3 ml acetic acid with 25 mg of 10% palladium on carbon catalyst at atmospheric pressure was stopped when 1.1 equivalent of hydrogen had been absorbed. The solution was filtered and the flask and catalyst washed with 5 ml of methanol. The methanol was evaporated under vacuum and the remaining solution was poured into a solvent comprising 15 ml of water and 15 ml of ether, and cooled to 0° C. Concentrated ammonia was added dropwise with vigorous stirring until the aqueous layer was basic. The organic layer was separated, washed with water and brine, dried ($Na_2SO_4$) and concentrated to 114 mg of white foam which yielded I-f', 104 mg (90% yield) of white crystals from ether. An analytical sample recrystallized from ether/hexane had: mp 127°-129° C.; NMR ($CDCl_3$) $\delta 9.37$ (1H, bs), 7.60-6.94 (4H, m), 3.86 (3H, s), 3.54 (1H, bs), 3.34-3.08 (2H, m), 2.80-2.30 (3H, m), 2.06-1.52 (3H, m), 1.12-0.86 (5H, m); IR (KBr) $\nu_{max}^{cm}{}_{-1}$ 3290, 3220, 2920, 2850, 1665, 1590, 1240, 1195, 730; UV (MeOH) $\lambda_{max}$ 230, 300, 330 nm; mass spectrum (80 eV) m/e (%) 298 (100), 255 (63), 216 (59), 215 (92), 214 (70), 167 (46), 154 (64), 84 (74).

Anal. Calcd. for $C_{18}H_{22}N_2O_2$: C, 72.45%; H, 7.43%; N, 9.39%. Found: C, 72.52%; H, 7.36%; N, 9.42%.

EXAMPLE 22 methyl,3-benzyl,1,2,3,3a,4,5-hexahydro-4,4,-spirocyclohexyl-7H-pyrrolo(2,3-d)carbazole-6-carboxylate, hereafter referred to as "I-g".

16.54 g (0.147 M) of cyclohexanecarboxaldehyde was added to a suspension of 30 g of an azepinoindole, Formula V wherein $R_4=CH_3$, $R_5=R_6=H$, and 0.4 g of benzoic acid in 500 ml of anhydrous methanol. The reaction mixture was stirred at room temperature under argon for 22 hours. Disappearance of the starting material was monitored by tlc and formation of a major product (hereafter referred to as "II-g") was observed. The solvent and excess aldehyde were removed in vacuo. The residue was dissolved in 450 ml of anhydrous $CHCl_3$. 23.14 g (0.135 M) of benzyl bromide and 30 ml of diisopropylethylamine were added. The reaction mixture was refluxed and monitored by tlc. After 48 h, an additional 4.86 ml of benzyl bromide and 4 ml of diisopropylethylamine were added and the reflux maintained for 72 h. The solvent and the excess organic base were removed and the residue was treated with 200 ml of a saturated aqueous solution of $K_2CO_3$, and 400 ml of dichloromethane. The organic phase was separated and the aqueous layer was extracted twice with dichloromethane. The combined organic phases were washed with 300 ml of water and 300 ml of brine and dried over $MgSO_4$. The solvent was removed under reduced pressure to afford an oil which crystallized in methanol. 41.9 g of product I-g was isolated (yield 79%): mp: 168° C.; mass spectrum: 428 (M+, 35%), 332 (39%), 214 (100%); IR ($CHCl_3$, 3%) 3390, 3000, 2930, 1670, 1641, 1608, 1463, 1437 cm$^{-1}$; UV ($CH_3OH$): 331 (4.25), 300 (4.06), 226 (4.02).

I claim:

1. A compound of the formula

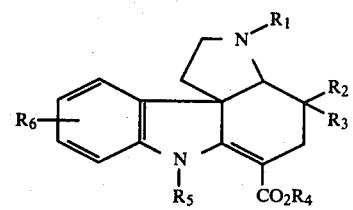

wherein $R_1$ and $R_5$ each represents hydrogen, lower alkyl, or benzyl;

$R_2$ and $R_3$ each represents hydrogen or lower alkyl or, together, lower alkylene;

$R_4$ is lower alkyl;

$R_6$ is hydrogen, nitro, lower alkoxy, halo or hydroxy; or an addition salt of said compound.

2. A compound as claimed in claim 1 wherein $R_5$ represents hydrogen or lower alkyl.

3. A compound as claimed in claim 1 wherein said lower alkyl or alkyloxy group has no greater than about 5 carbons.

4. Methyl 4-ethyl-1,2,3,3a,4,5-hexahydro-7H-pyrrolo(2,3-d)carbazole-6-carboxylate or an addition salt thereof, as claimed in claim 1.

5. Methyl 1,2,3,3a,4,5-hexahydro-7H-pyrrolo(2,3-d)carbazole-6-carboxylate or an addition salt thereof, as claimed in claim 1.

6. Methyl 3-benzyl-1,2,3,3a,4,5-hexahydro-7H-pyrrolo(2,3-d)carbazole-6-carboxylate or an addition salt thereof, as claimed in claim 1.

7. Methyl 1,2,3,3a,4,5-hexahydro-4-methyl-7H-pyrrolo(2,3-d)carbazole-6-carboxylate or an addition salt thereof, as claimed in claim 1.

8. Methyl 1,2,3,3a,4,5-hexahydro-4,4-dimethyl-7H-pyrrolo(2,3-d)carbazole-6-carboxylate or an addition salt thereof, as claimed in claim 1.

9. Methyl 3-benzyl-4-ethyl-1,2,3,3a,4,5-hexahydro-7H-pyrrolo(2,3-d)carbazole-6-carboxylate or an addition salt thereof, as claimed in claim 1.

10. Methyl 3-ethyl-1,2,3,3a,4,5-hexahydro-4,4-dimethyl-7H-pyrrolo(2,3-d)carbazole-6-carboxylate or a salt thereof, as claimed in claim 1.

11. Methyl 1,2,3,3a,4,5-hexahydro-3,4,4-trimethyl-7H-pyrrolo(2,3-d)carbazole-6-carboxylate or a salt thereof, as claimed in claim 1.

12. Methyl 3-benzyl-1,2,3,3a,4,5-hexahydro-4,4-dimethyl-7H-pyrrolo(2,3-d)carbazole-6-carboxylate or a salt thereof, as claimed in claim 1.

13. Methyl 3-benzyl-1,2,3,3a,4,5-hexahydro-4-methyl-7H-pyrrolo(2,3-d)carbazole-6-carboxylate or a salt thereof, as claimed in claim 1.

14. Methyl,3-benzyl,1,2,3,3a,4,5-hexahydro-4,4-spirocyclohexyl-7H-pyrrolo(2,3-d)carbazole-6-carboxylate or an addition salt thereof, as claimed in claim 1.

15. A pharmaceutical composition comprising a compound, as claimed in claim 1, 2 or 3, in the form of the base or in the form of an acid addition salt of a pharmaceutically acceptable acid, and including also a pharmaceutically acceptable carrier.

16. A pharmaceutical composition comprising a compound of claim 4, 5, 6, 7, 8, 9, 10, 11, 12 or 13 in the form of an acid addition salt of a pharmaceutically acceptable acid, and including also a pharmaceutically acceptable carrier.

17. A composition, as claimed in claim 15, wherein the amount of said compound or said salt is about 0.5 to about 700 mg.

18. In the therapeutic treatment of epileptic, cerebral-vascular or cardio-circulatory afflictions, the improvement comprising the administration to or ingestion by the afflicted of a therapeutically effective amount of a compound or salt as claimed in claim 1–12, or 13.

19. A therapeutic treatment, as claimed in claim 17, wherein said compound or said salt is administered or ingested in a daily amount of about 1 to about 500 mg.

* * * * *